(12) United States Patent
Tseng et al.

(10) Patent No.: US 10,934,315 B2
(45) Date of Patent: Mar. 2, 2021

(54) PROCESS FOR PREPARING BORTEZOMIB, INTERMEDIATES, AND CRYSTALLINE FORMS THEREOF

(71) Applicant: PHARMACORE BIOTECH CO., LTD., Tainan (TW)

(72) Inventors: Wei-Hong Tseng, Tainan (TW); Vallapa Soong, Tainan (TW); Hsing Yu Chang, Tainan (TW); Shen Han Yang, Tainan (TW)

(73) Assignee: PHARMACORE BIOTECH CO., LTD., Tainan (TW)

( * ) Notice: Subject to any disclaimer, the term of this patent is extended or adjusted under 35 U.S.C. 154(b) by 0 days.

(21) Appl. No.: 16/177,499

(22) Filed: Nov. 1, 2018

(65) Prior Publication Data
US 2020/0140464 A1  May 7, 2020

(51) Int. Cl.
*C07D 241/24* (2006.01)
*C07F 9/6571* (2006.01)
*C07F 9/38* (2006.01)
*C07F 5/02* (2006.01)
*B01D 9/00* (2006.01)

(52) U.S. Cl.
CPC .............. *C07F 5/025* (2013.01); *B01D 9/005* (2013.01); *C07D 241/24* (2013.01)

(58) Field of Classification Search
CPC .................................................... C07D 241/24
See application file for complete search history.

(56) References Cited

U.S. PATENT DOCUMENTS 8,884,009 B2 * 11/2014 Castulik ............... C07D 241/24
544/229

* cited by examiner

*Primary Examiner* — Alexander R Pagano
*Assistant Examiner* — Ebenezer O Sackey
(74) *Attorney, Agent, or Firm* — WPAT, PC

(57) ABSTRACT

The present disclosure provides a process for preparing Bortezomib, intermediates, and crystalline forms thereof.

8 Claims, 9 Drawing Sheets

PROCESS FOR PREPARING BORTEZOMIB, INTERMEDIATES, AND CRYSTALLINE FORMS THEREOF

BACKGROUND OF THE INVENTION

1. Field of the Invention

The present invention relates to a process for preparing Bortezomib. In particular, the present invention relates to a process for preparing Bortezomib, intermediates, and crystalline forms thereof.

2. The Prior Art

Bortezomib is a modified dipeptidyl boronic acid derivative derived from leucine and phenylalanine. The chemical name is [(1R)-3-methyl-1-[[(2S)-1-oxo-3-phenyl-2-[(pyrazinylcarbonyl)amino]propyl]amino]butyl] boronic acid and represented as follows:

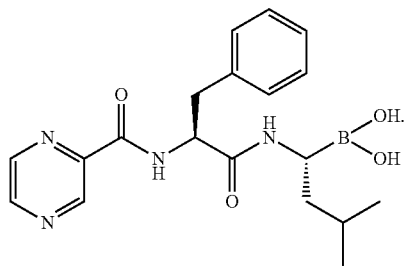

Formula V

Bortezomib is cytotoxic to a variety of cancer cell types in vitro and causes a delay in tumor growth in vivo in nonclinical tumor models, including multiple myeloma. Bortezomib presently is approved in USA for the treatment of multiple myeloma, relapsed multiple myeloma, and mantle cell lymphoma. A variety of combination therapies have been investigated for treating multiple myeloma, in which Bortezomib is administered with one or more other biologically active substances, such as lenalidomide, dexamethasone, melphalan, predisone, thalidomide, cyclophosphamide, doxorubicin, vincristine, carmustine, pomalidomide, vorinostat, tanespimycin, and perifosine. Other potential uses of Bortezomib also have been reported, including treatment of amyloidosis.

Currently, there are various processes for the preparation and synthesis of Bortezomib. However, conventional processes require the use of halogenated solvents, solvent exchange and tedious work up procedures and hence, result in a poor yield.

Thus, there is a need to develop an industrially feasible, economically viable, commercially up-scalable process which may be safer for handling, less time consuming and which provides the product with improved yield and improved chemical purity.

SUMMARY OF THE INVENTION

A primary objective of the present invention is to provide a process for preparing Bortezomib, comprising the steps of:
(a) coupling a compound of formula I or its salt:

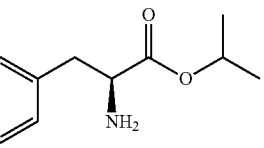

Formula I with a compound of formula II:

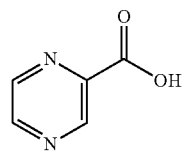

Formula II in the presence of a coupling agent and a base to provide a compound of formula III:

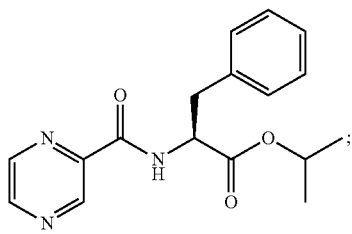

Formula III (b) converting the compound of formula III obtained in step (a) in the presence of the base to provide a compound of formula IV:

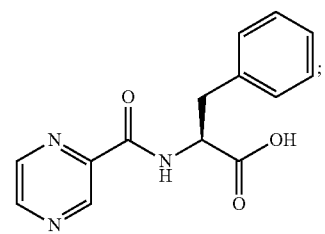

Formula IV (c) coupling the compound of formula IV obtained in step (b) with (1R)-3-methyl-1-[(3aS,4S,6S,7aR)-3a5,5-trimethylhexahydro-4,6 methano-1,3,2-benzodioxaborol-2-yl]butan-1-amine or its salt in the presence of the coupling agent and the base to provide an intermediate of (N-[(1 S)-2-[[(1R)-1-[(3aS,4S,6S,7aR)-hexahydro-3a,5,5-trimethyl-4,6-methano-1,3,2-benzodioxaborol-2-yl]-3-methylbutylamino]-2-oxo-1-(phenylmethyl)ethyl] pyrazinecarboxamide without isolation; and (d) converting the intermediate obtained in step (c) with 0.44N to 3.1N acid based on the weight of the compound of formula IV to provide a compound of formula V:

Formula V

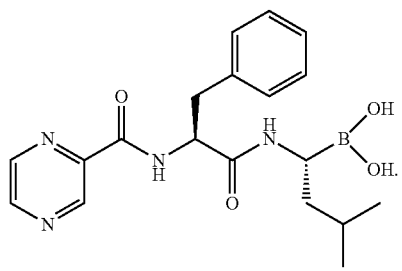

According to an embodiment of the present invention, the coupling agent is selected from the group consisting of 2-(1H-benzotriazol-1-yl)-1,1,3,3-tetramethyluronium tetrafluoroborate (TBTU), O-benzotriazole-N,N,N',N'-tetramethyluronium-hexafluoro-phosphate (HBTU), 2-(6-chloro-1H-benzotriazole-1-yl)-1,1,3,3-tetramethylaminium hexafluorophosphate (HCTU), N-(3-dimethylaminopropyl)-N'-ethylcarbodiimide hydrochloride (EDC), and dicyclohexylcarbodiimide (DCC).

According to an embodiment of the present invention, the base in solid, liquid or aqueous form is N,N-diisopropylethylamine (DIPEA).

According to an embodiment of the present invention, the acid in step (d) is selected from the group consisting of an organic boronic acid and aqueous hydrochloric acid According to an embodiment of the present invention, a mole ratio of thionyl chloride to the compound of formula I is 1.5 to 3.0.

According to an embodiment of the present invention, a mole ratio of the base to the compound of formula IV is 1.5 to 3.0.

According to an embodiment of the present invention, a temperature of the step (a) is preferably from about −15 to 10° C.

According to an embodiment of the present invention, the compound of formula V has a purity level greater than 99.6% by HPLC.

According to an embodiment of the present invention, the compound of formula V comprises less than 0.1% of S,S-isomer and R,R-isomer.

Another objective of the present invention is to provide a process for preparing crystalline form D of the Bortezomib obtained from the abovementioned process, comprising dissolving the compound of formula V in a solution comprising dichloromethane and tert-butyl methyl ether.

According to an embodiment of the present invention, the crystalline form D of the compound of formula V is characterized by X-ray powder diffraction pattern comprising the characteristic 2θ° peaks of 4.4, 5.2, 6.5, 8.8, 9.3, 10.2, 12.0, 14.5, 18.1, 19.8, 22.1 and 24.1±0.2°, wherein peaks at 4.4 and 18.1±0.2° are un-split and 100% intensity peak is present at 6.5±0.2°, infrared absorption spectrum comprising the characteristic peaks approximately at 3311 $cm^{-1}$, 2952 $cm^{-1}$, 1682 $cm^{-1}$, 1653 $cm^{-1}$, and 1511 $cm^{-1}$, and exhibits a melting point at 148±2° C. in differential scanning calorimetry (DSC).

According to an embodiment of the present invention, the X-ray powder diffraction pattern of the crystalline form D of the compound of formula V is substantially in accordance with FIG. 1, the infrared absorption spectrum of the crystalline form D of the compound of formula V is substantially in accordance with FIG. 2 and the differential scanning calorimetry in accordance with FIG. 3

Another objective of the present invention is to provide a process for preparing crystalline form E of the Bortezomib obtained from the abovementioned process, comprising the steps of: (a) dissolving the compound of formula V in a solution comprising dichloromethane at 30-39° C.; (b) adding tert-butyl methyl ether and cooling to 0-10° C.; and (c) isolating the crystalline form E of the Bortezomib in solid state.

According to an embodiment of the present invention, the crystalline form E of the compound of formula V is characterized by X-ray powder diffraction pattern comprising the characteristic 2θ° peaks of 6.0, 8.5, 12.2, 18.2, 20.2, and 24.2±0.2°, wherein peaks at 6.0±0.20 are un-split and 100% intensity peak is present at 6.0±0.2°, infrared absorption spectrum comprising the characteristic peaks approximately at 3337 $cm^{-1}$, 2950 $cm^{-1}$, 1681 $cm^{-1}$, 1649 $cm^{-1}$, and 1507 $cm^{-1}$ and exhibits melting points at 150±2° C. and 183±2° C. in differential scanning calorimetry (DSC).

According to an embodiment of the present invention, the X-ray powder diffraction pattern of the crystalline form E of the compound of formula V is substantially in accordance with FIG. 4, and the infrared absorption spectrum of the crystalline form E of the compound of formula V is substantially in accordance with FIG. 5 and the differential scanning calorimetry in accordance with FIG. 6.

Another objective of the present invention is to provide a process for preparing a crystalline form of the Bortezomib obtained from the abovementioned process, comprising the steps of: (a) dissolving the compound of formula V in a solution comprising tetrahydrofuran at 30-40° C.; (b) cooling to 0 to −20° C. to precipitate a solid; and (c) isolating the solid which is the crystalline form of the compound of formula V.

According to an embodiment of the present invention, the crystalline form of the compound of formula V is the crystalline form F of the Bortezomib, and is characterized by X-ray powder diffraction pattern comprising the characteristic 2θ° peaks of 4.2, 5.4, 7.1, 8.5, 9.5, 10.8, 13.5, 18.0, 19.0, and 19.6±0.2°, wherein peaks at 4.2 and 5.4±0.2° are un-split and 100% intensity peak is present at 5.4±0.20, infrared absorption spectrum comprising the characteristic peaks approximately at 3267 $cm^{-1}$, 2952 $cm^{-1}$, 1660 $cm^{-1}$, 1511 $cm^{-1}$, and 1019 $cm^{-1}$, and exhibits a melting point at 121±2° C. in differential scanning calorimetry (DSC).

According to an embodiment of the present invention, the X-ray powder diffraction pattern of the crystalline form F of the compound of formula V is substantially in accordance with FIG. 7, the infrared absorption spectrum of the crystalline form F of the compound of formula V is substantially in accordance with FIG. 8 and the differential scanning calorimetry in accordance with FIG. 9.

Accordingly, the advantageous effect of the present invention is to provide an industrially feasible, economically viable, commercially up-scalable process which may be safer for handling, less time consuming and which provides the product with improved yield and improved chemical purity.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
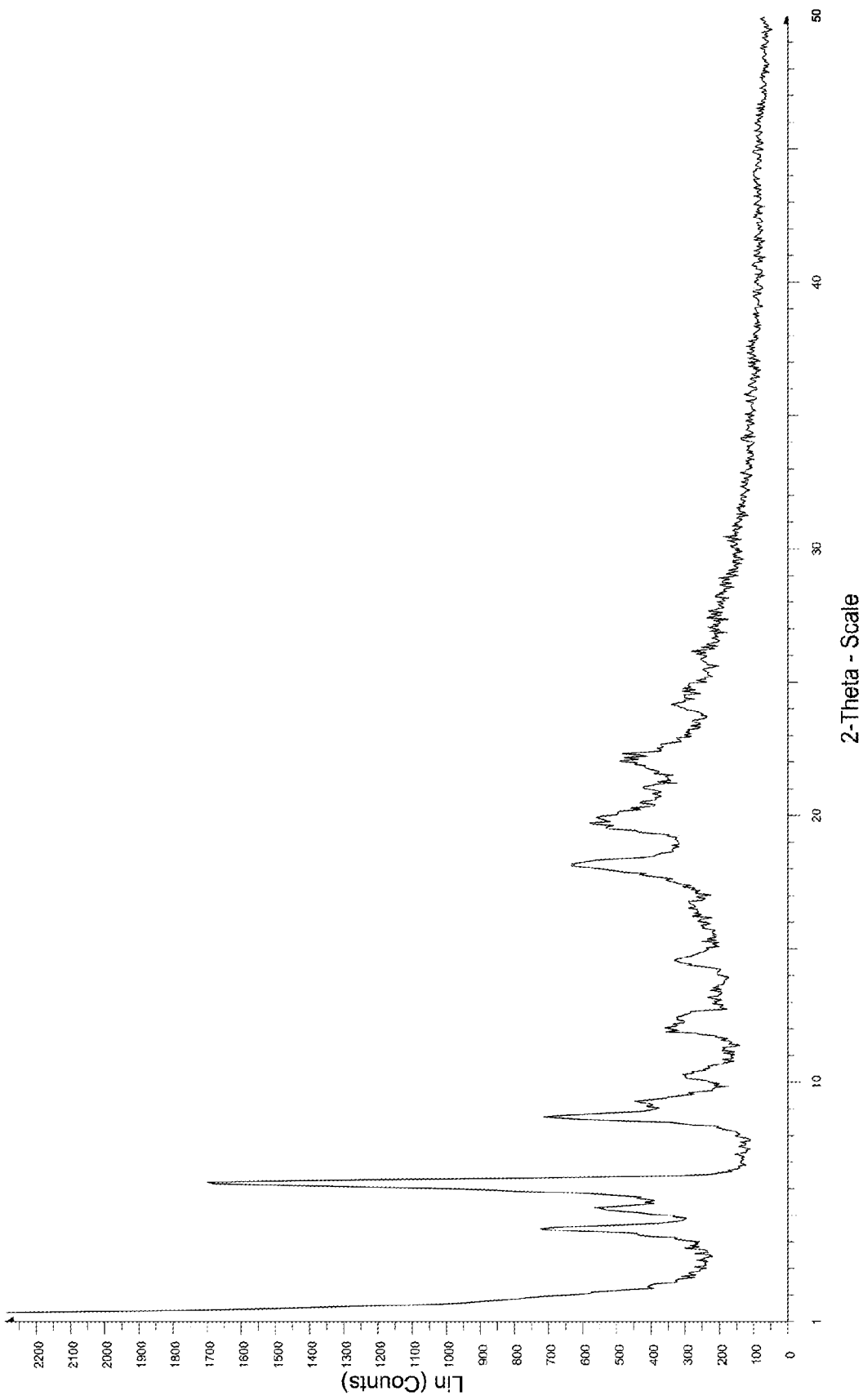
FIG. 1 shows the X-ray powder diffraction pattern of the crystalline form D of Bortezomib.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

The purity of the solid forms provided herein may be determined by standard analytical methods, such as thin layer chromatography (TLC), gel electrophoresis, gas chromatography, ultra-high performance liquid chromatography (UHPLC), and mass spectrometry (MS).

It should be understood that the numerical values of the peaks of an X-ray powder diffraction pattern may vary slightly from one machine to another or from one sample to another, and so the values quoted are not to be construed as absolute, but with an allowable variability, such as .+-.0.0.2.degree. 2.theta. or .+-.0.0.1.degree. 2.theta. (see United State Pharmacopoeia, page 2228 (2003)).

The complete synthetic route of Bortezomib is shown in the following scheme:

Scheme

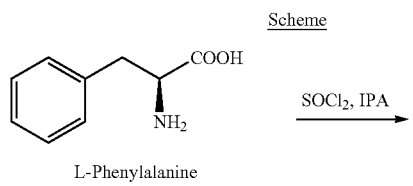

L-Phenylalanine

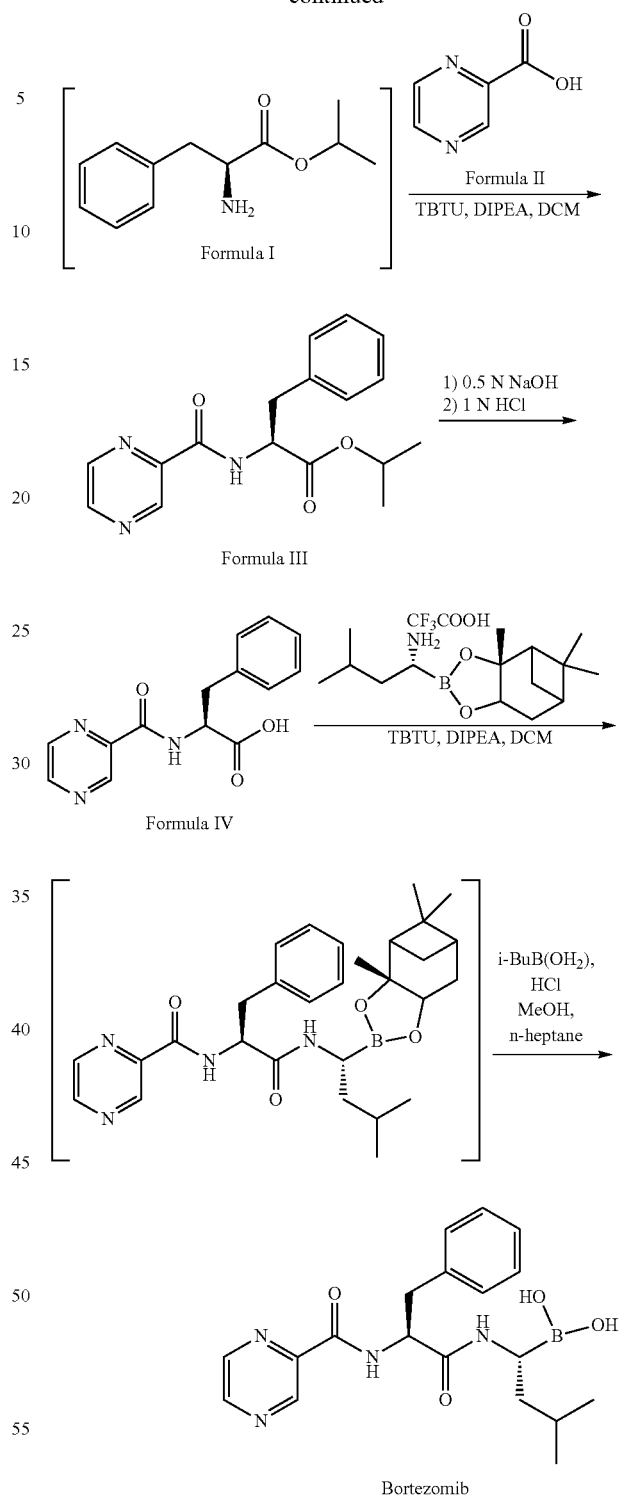

Example 1 Preparation of Bortezomib and its Intermediates

L-phenylalanine represented as follows was provided and converted to L-phenylalanine isopropyl ester of formula I or its salt:

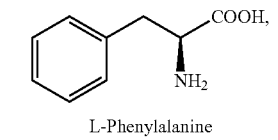

L-Phenylalanine

Formula I

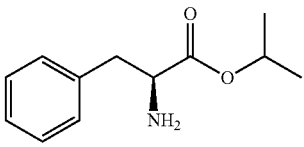

in the presence of 1.5 to 3.0 equivalent of thionyl chloride (SOCl$_2$) and isopropyl alcohol (IPA). Subsequently, the L-phenylalanine isopropyl ester of formula I or its salt was coupled with 1.1 to 1.3 equivalent of pyrazine-2-carboxylic acid of formula II:

Formula II

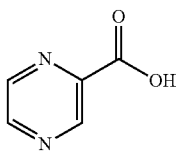

in the presence of a coupling agent (i.e., TBTU), a base (i.e., N,N-diisopropylethylamine, DIPEA), and a solvent (i.e., dichloromethane, DCM) to provide a compound of formula III:

Formula III

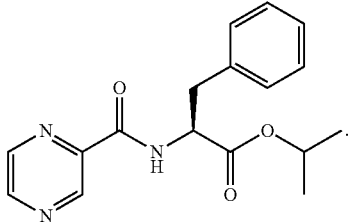

In particular, a temperature of the aforesaid process is preferably from about −15 to 10° C.

Thereafter, the compound of formula III was converted to a compound of formula IV:

Formula IV

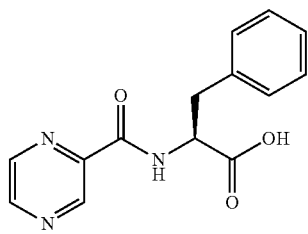

in the presence of the base (i.e., 0.5N sodium hydroxide) and 1N hydrochloric acid. The compound of formula IV was coupled with (1R)-3-methyl-1-[(3aS,4S,6S,7aR)-3a5,5-trimethylhexahydro-4,6 methano-1,3,2-benzodioxaborol-2-yl]butan-1-amine represented as follows or its salt:

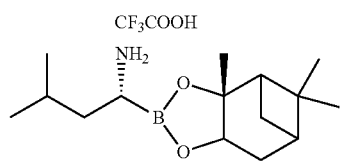 [SMILES: CC(C)C[C@H](N)B1OC2CC3CC(C3(C)C)[C@@]2(C)O1 ; "CF3COOH"]

in the presence of TBTU, DIPEA and DCM to provide an intermediate of (N-[(1S)-2-[[(1R)-1-[(3aS,4S,6S,7aR)-hexahydro-3a,5,5-trimethyl-4,6-methano-1,3,2-benzodioxaborol-2-yl]-3-methylbutylamino]-2-oxo-1-(phenylmethyl)ethyl]pyrazinecarboxamide represented as follows without isolation:

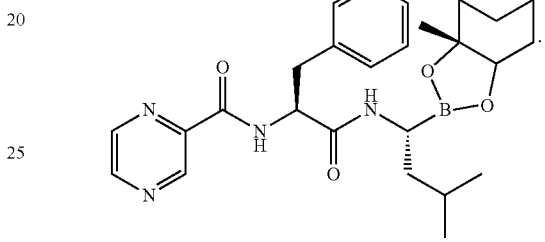

Thereafter, the intermediate was converted to compound of formula V:

Formula V

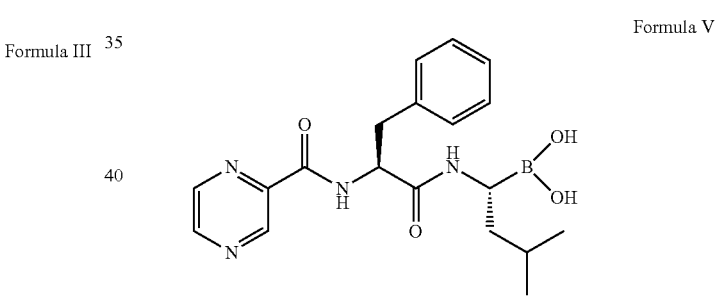

in the presence of i-BuB(OH)$_2$, 12 volume of 0.44N to 3.1N hydrochloric acid based on the weight of the compound of formula IV, methanol, and n-heptane.

The yield of the compound of formula III is 95%, and the HPLC purity of the compound of formula III is greater than 99.7%. The yield of the compound of formula IV is 90%, and the HPLC purity of the compound of formula IV is greater than 99.5%. The obtained Bortezomib has purity level greater than 99.6% by HPLC and contains less than 0.1% of S,S-isomer and R,R-isomer. In particular, a mole ratio of thionyl chloride to the compound of formula I is 1.5 to 3.0, and a mole ratio of the base to the compound of formula IV is 1.5 to 3.0.

Example 2 Preparation of Crystalline Forms of Bortezomib 2.1 Preparation of Crystalline Form D of Bortezomib The crystalline form D of Bortezomib was prepared by dissolving Bortezomib obtained in Example 1 in a solution comprising dichloromethane and tert-butyl methyl ether.

Figure 2:
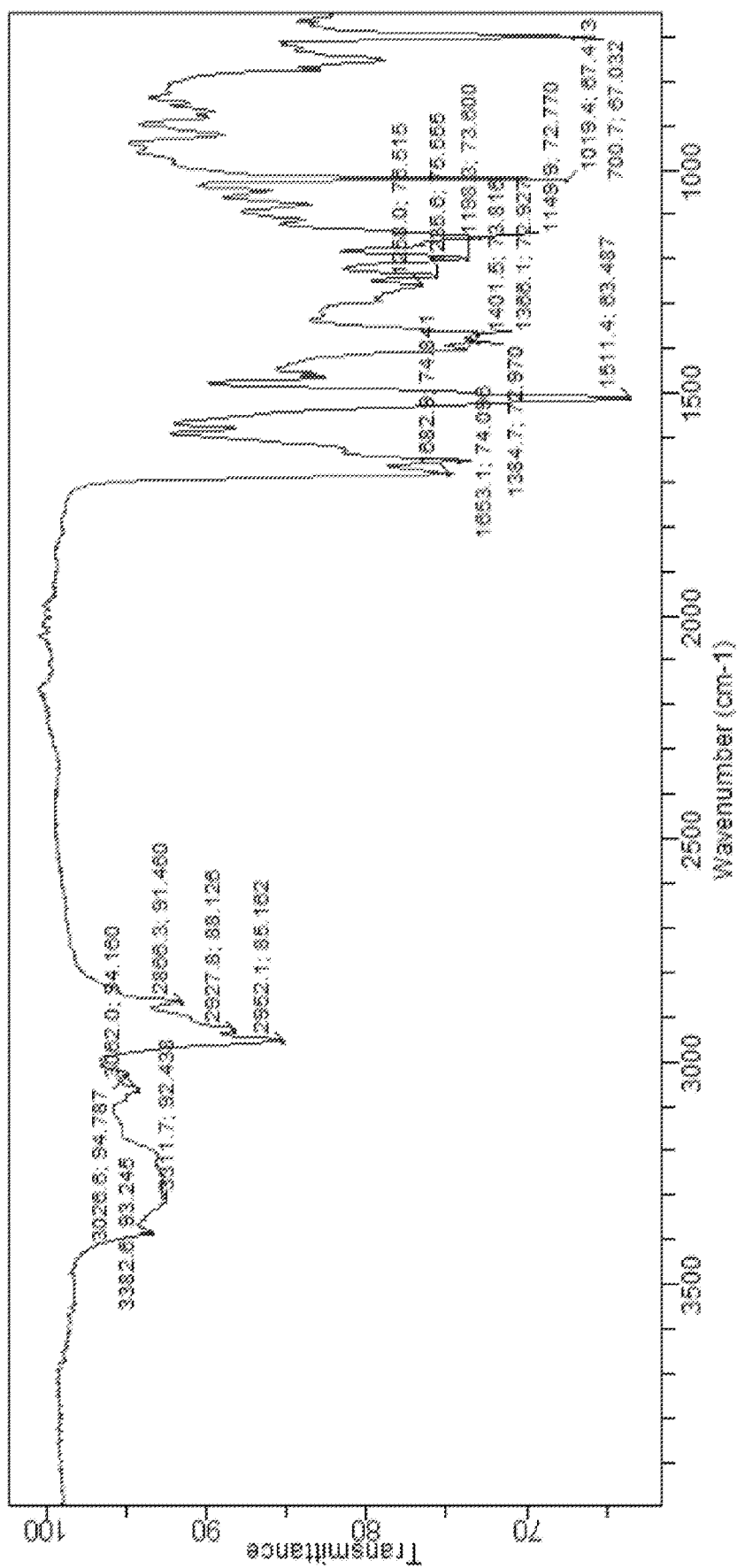
FIG. 2 shows the infrared absorption spectrum of the crystalline form D of Bortezomib.
Figure 3:
FIG. 3 shows the differential scanning calorimetry (DSC) of the crystalline form D of Bortezomib.

The X-ray powder diffraction pattern of the crystalline form D of Bortezomib is shown in FIG. 1, the infrared absorption spectrum of the crystalline form D of Bortezomib is shown in FIG. 2, and the differential scanning calorimetry (DSC) is shown in FIG. 3. As shown in FIG. 1, the crystalline form D of the Bortezomib is characterized by X-ray powder diffraction pattern comprising the characteristic 2θ° peaks of 4.4, 5.2, 6.5, 8.8, 9.3, 10.2, 12.0, 14.5, 18.1, 19.8, 22.1 and 24.1±0.2°, wherein peaks at 4.4 and 18.1±0.2° are un-split and 100% intensity peak is present at 6.5±0.20. As shown in FIG. 2, the crystalline form D of the Bortezomib is characterized by infrared absorption spectrum comprising the characteristic peaks approximately at 3311 $cm^{-1}$, 2952 $cm^{-1}$, 1682 $cm^{-1}$, 1653 $cm^{-1}$, and 1511 $cm^{-1}$. As shown in FIG. 3, the crystalline form D of the Bortezomib is characterized a melting point by the differential scanning calorimetry (DSC) at 148±2° C.

The crystalline form of bortezomib prepared in Example 2 was subjected to a stability test in a sealed state at a temperature of 0-10° C. for 3.5 months. As a result, it was shown that the crystalline from D of bortezomib was maintained in a stable state without any change in HPLC purity and crystalline form (Table 1).

TABLE 1

Form D of Formula V Stability at 0-10° C.

| | 1 week | 2 week | 1 month | 2 month | 3.5 month |
|---|---|---|---|---|---|
| Purity (%) | 99.61 | 99.87 | 99.80 | 99.74 | 99.69 |
| (S, S) and (R, R) diastereomer (%) | 0.068 | 0.042 | 0.046 | 0.039 | 0.048 |
| Form | D | D | D | D | D |

2.2 Preparation of Crystalline Form E of Bortezomib

The crystalline form E of Bortezomib was prepared by the following steps: (a) dissolving the Bortezomib about 1 g obtained in Example 1 in a solution comprising 100 mL dichloromethane at 30-39° C.; (b) adding 125 mL tert-butyl methyl ether and cooling to 0-10° C.; and (c) isolating the crystalline form E of the Bortezomib in solid state.

Figure 4:
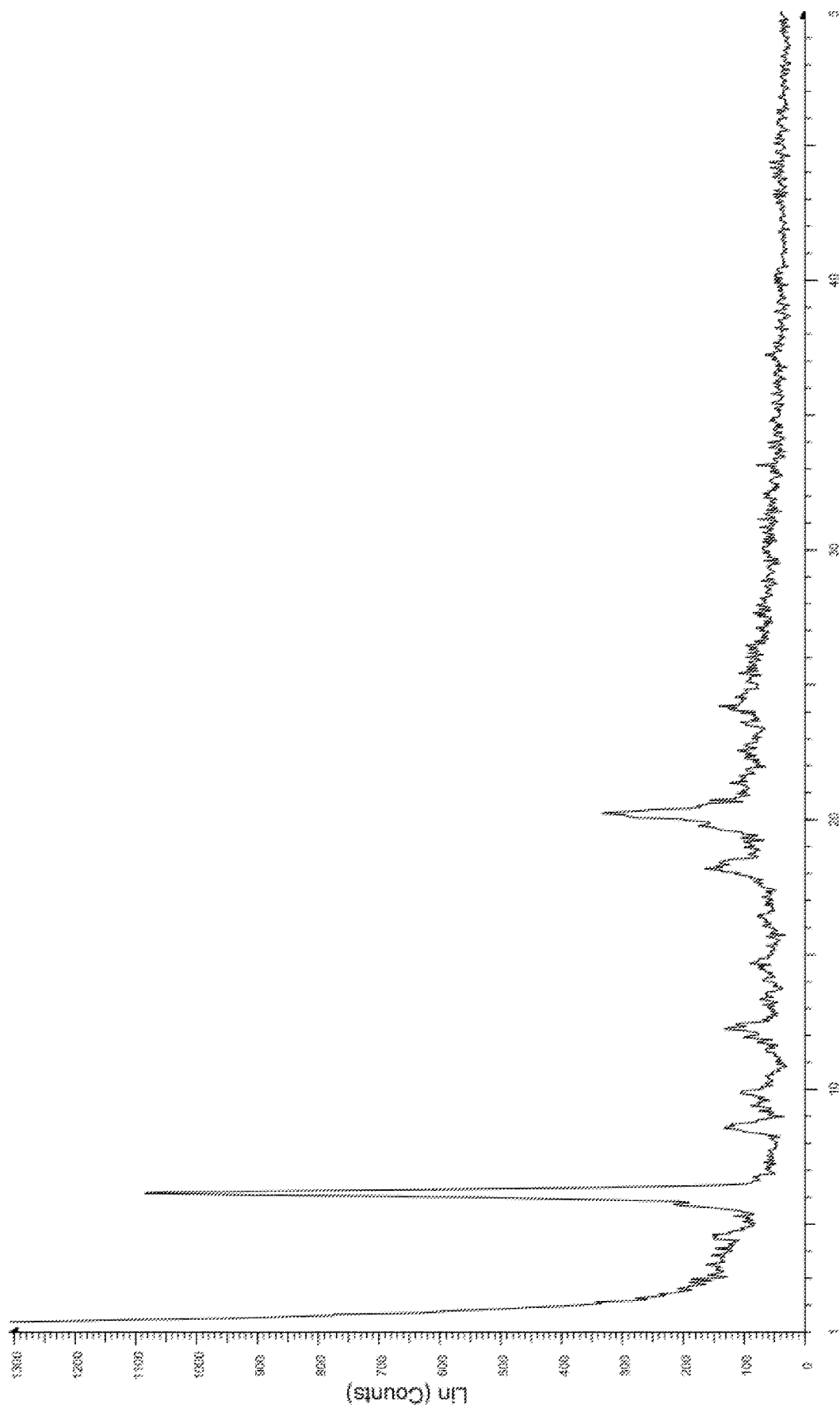
FIG. 4 shows the X-ray powder diffraction pattern of the crystalline form E of Bortezomib.
Figure 5:
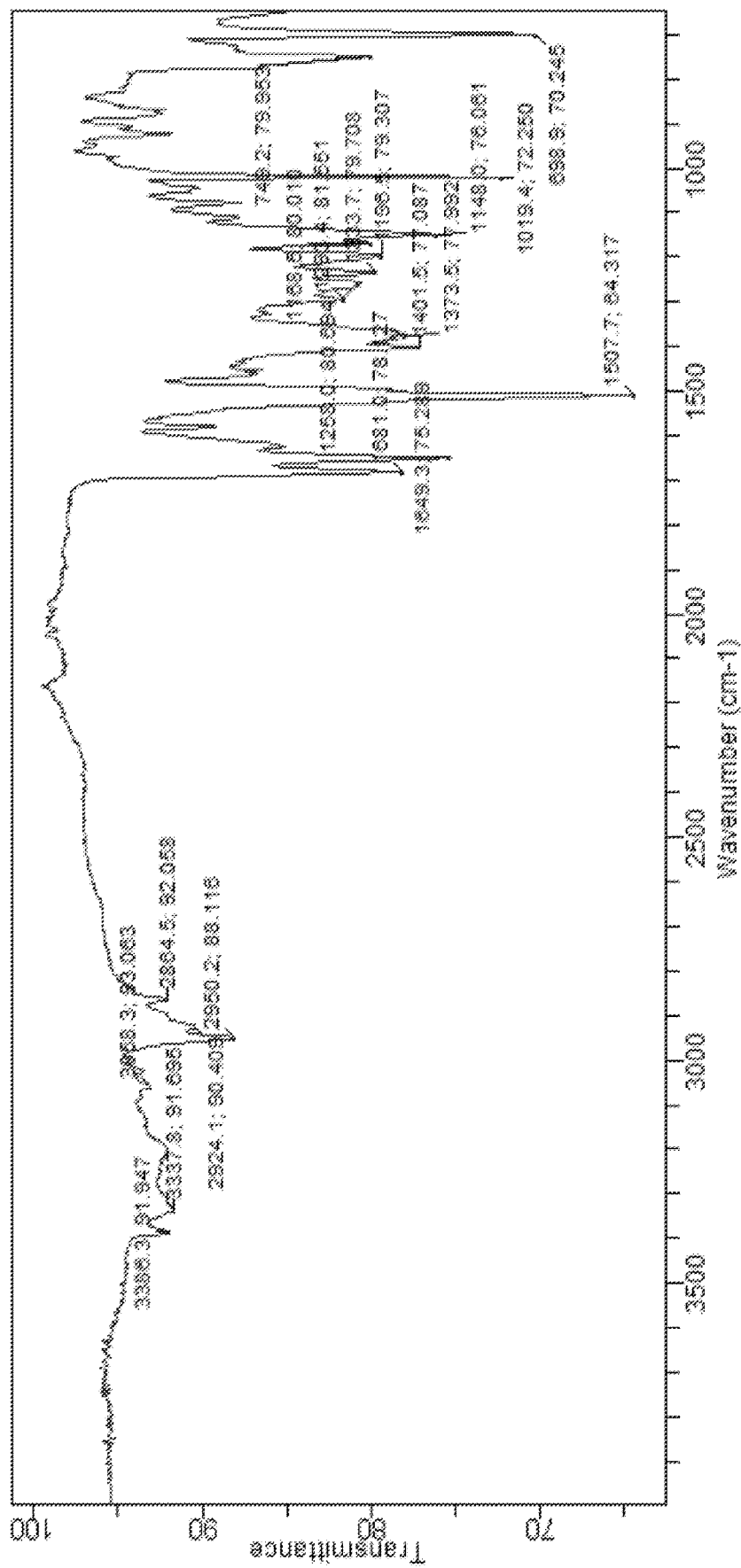
FIG. 5 shows infrared absorption spectrum of the crystalline form E of Bortezomib.
Figure 6:
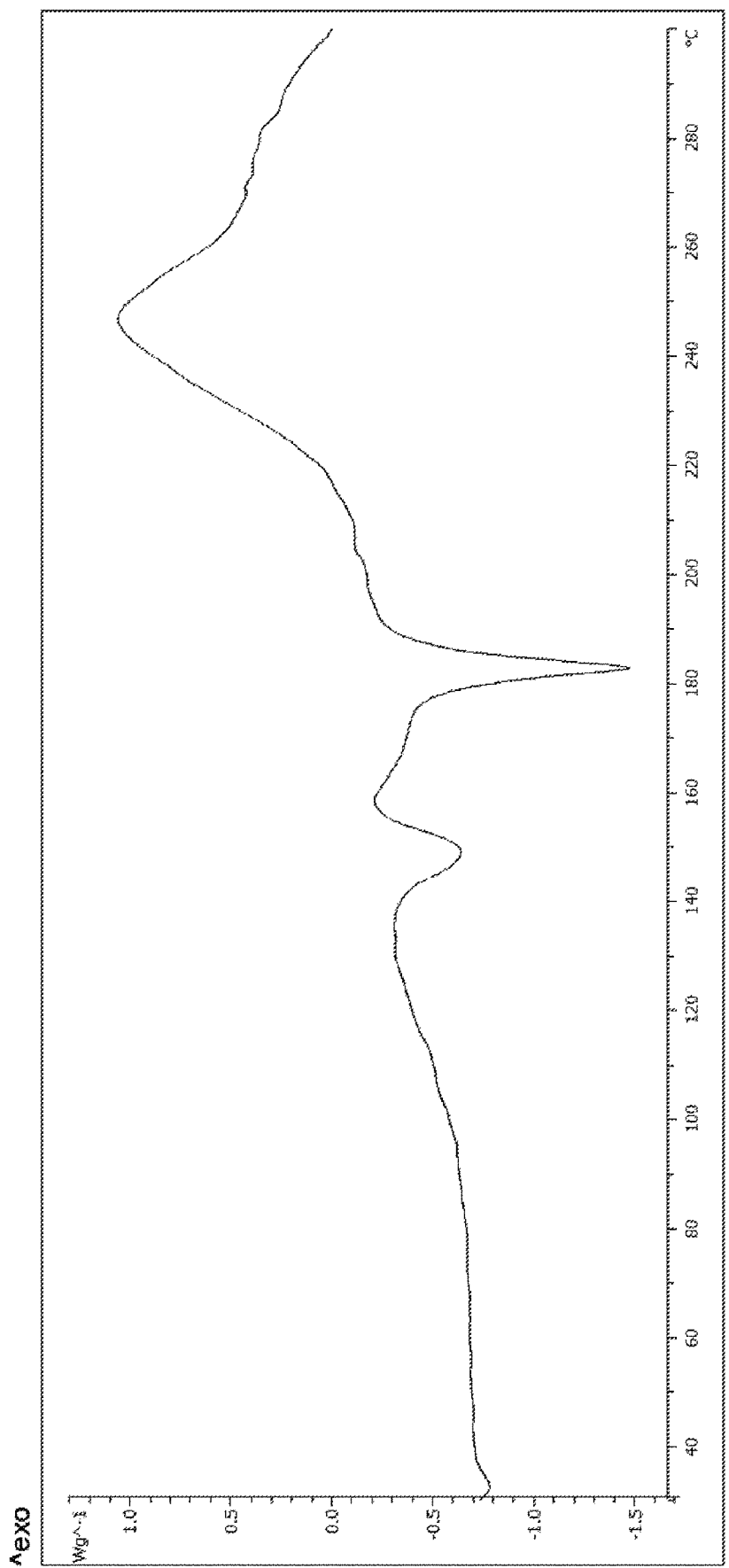
FIG. 6 shows the differential scanning calorimetry (DSC) of the crystalline form E of Bortezomib.

The X-ray powder diffraction pattern of the crystalline form E of Bortezomib is shown in FIG. 4, the infrared absorption spectrum of the crystalline form E of Bortezomib is shown in FIG. 5, and the differential scanning calorimetry (DSC) is shown in FIG. 6. As shown in FIG. 4, the crystalline form E of the Bortezomib is characterized by X-ray powder diffraction pattern comprising the characteristic 2θ° peaks of 6.0, 8.5, 12.2, 18.2, 20.2, and 24.2±0.2°, wherein peaks at 6.0±0.2° are un-split and 100% intensity peak is present at 6.0±0.20. As shown in FIG. 5, the crystalline form E of the Bortezomib is characterized by infrared absorption spectrum comprising the characteristic peaks approximately at 3337 $cm^{-1}$, 2950 $cm^{-1}$, 1681 $cm^{-1}$, 1649 $cm^{-1}$, and 1507 $cm^{-1}$. As shown in FIG. 6, the crystalline form E of the Bortezomib is characterized a melting point by the differential scanning calorimetry (DSC) at 150±2° C. and 183±2° C.

2.3 Preparation of Crystalline Form F of Bortezomib

The crystalline form F of Bortezomib was prepared by the following steps: (a) dissolving the Bortezomib obtained in Example 1 in a solution comprising tetrahydrofuran at 30-40° C.; (b) cooling to 0--20° C. to precipitate a solid; and (c) isolating the solid which is the crystalline form F of the Bortezomib.

Figure 7:
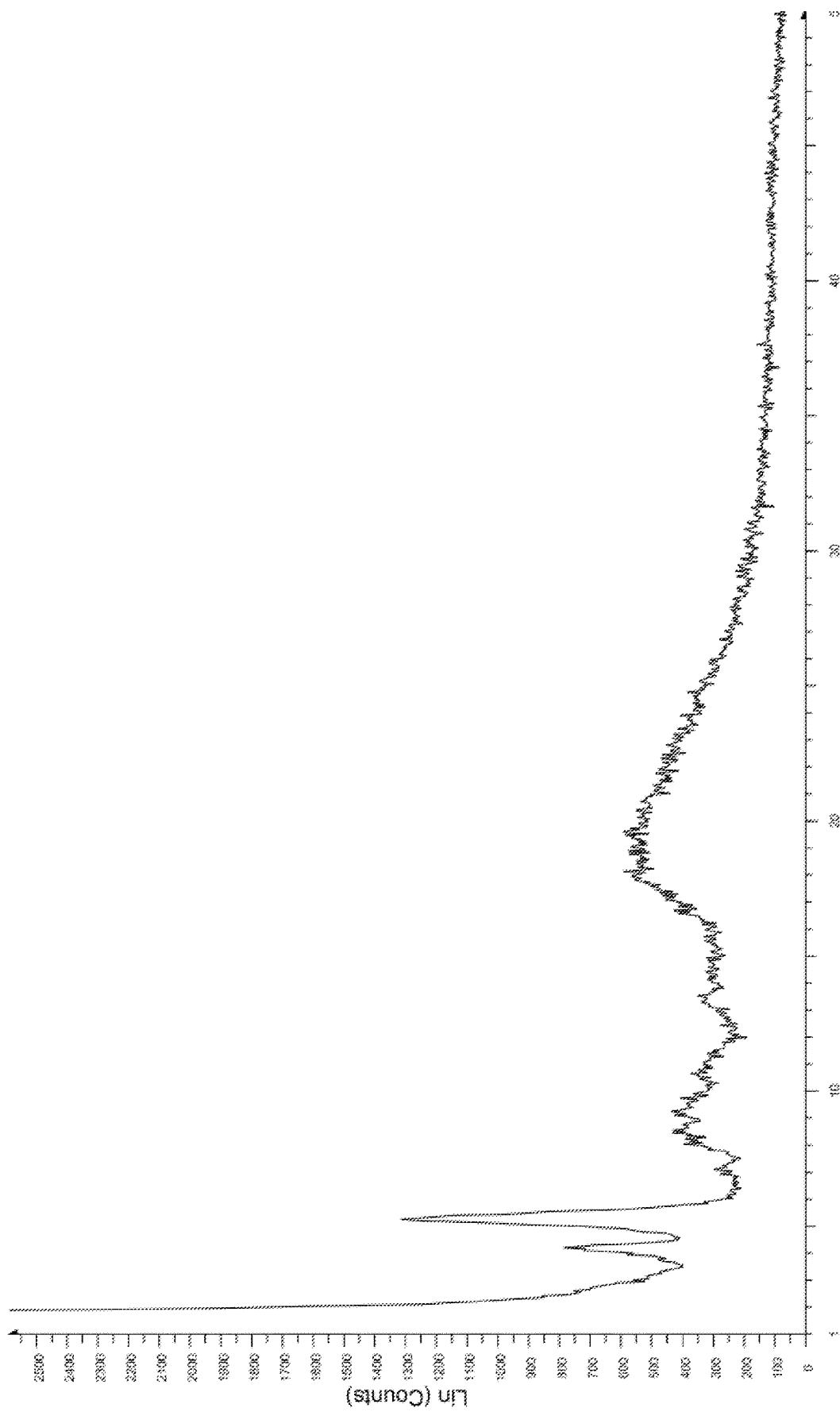
FIG. 7 shows the X-ray powder diffraction pattern of the crystalline form F of Bortezomib.
Figure 8:
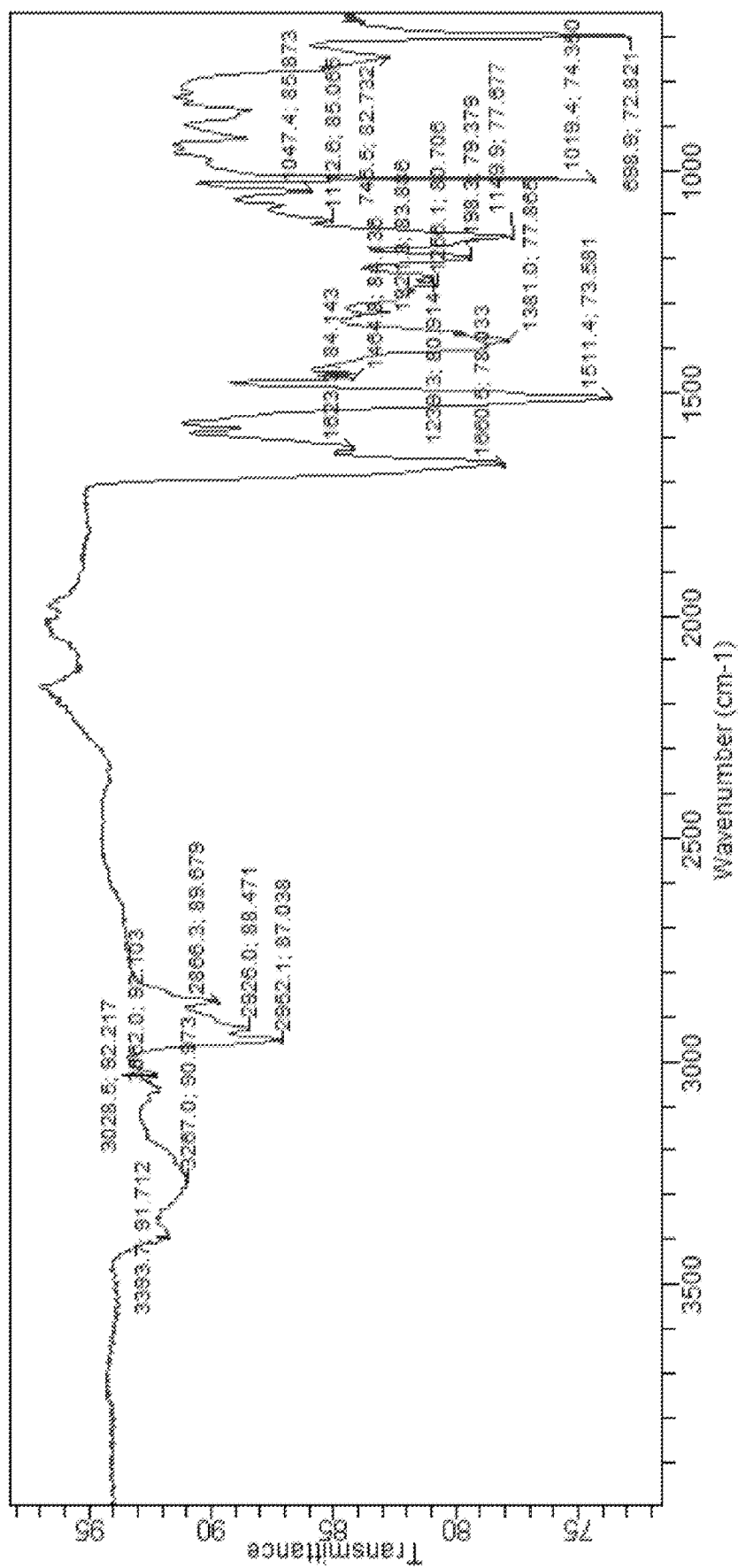
FIG. 8 shows the infrared absorption spectrum of the crystalline form F of Bortezomib.
Figure 9:
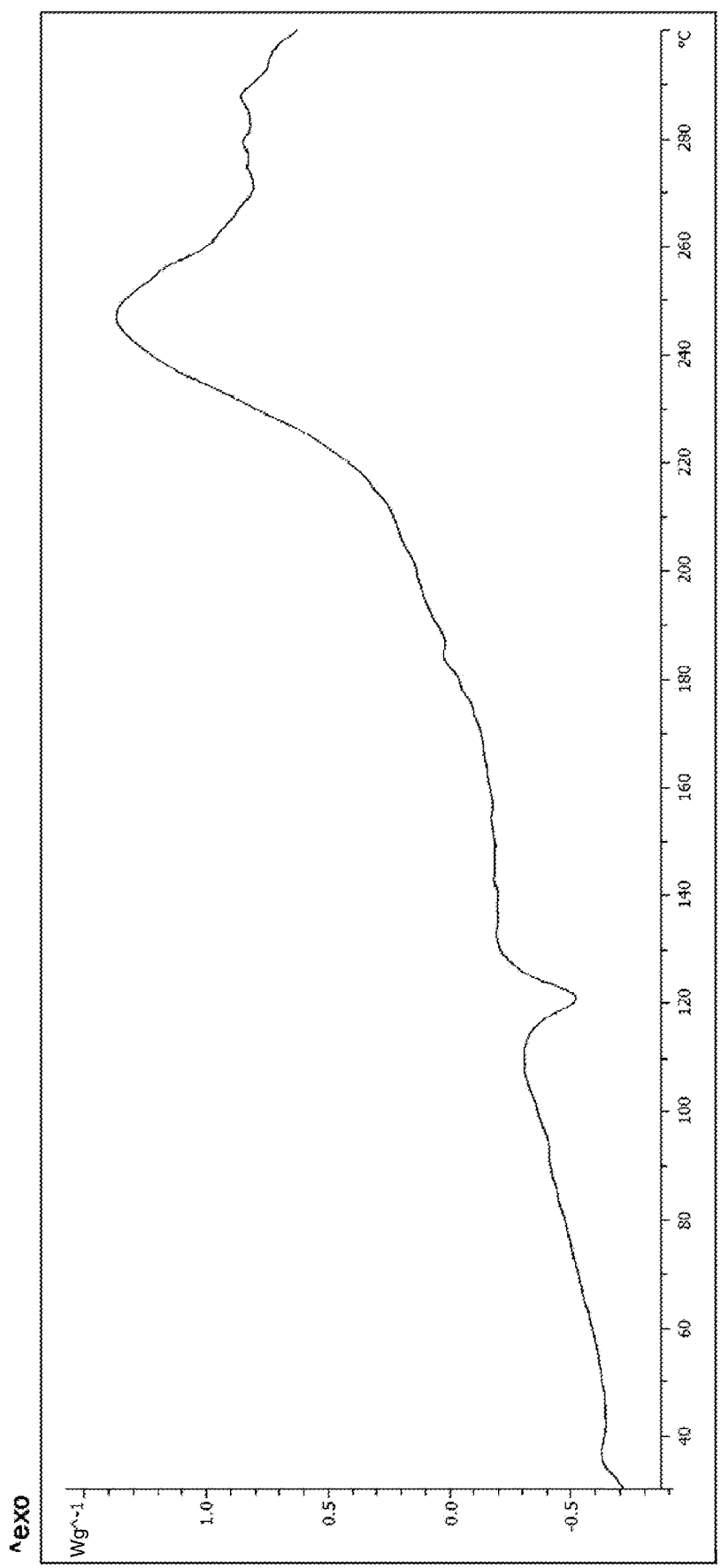
FIG. 9 shows the differential scanning calorimetry (DSC) of the crystalline form F of Bortezomib.

The X-ray powder diffraction pattern of the crystalline form F of Bortezomib is shown in FIG. 7, the infrared absorption spectrum of the crystalline form F of Bortezomib is shown in FIG. 8 and the differential scanning calorimetry (DSC) is shown in FIG. 9. As shown in FIG. 7, the crystalline form F of the Bortezomib is characterized by X-ray powder diffraction pattern comprising the characteristic 2θ° peaks of 4.2, 5.4, 7.1, 8.5, 9.5, 10.8, 13.5, 18.0, 19.0, and 19.6±0.2°, wherein peaks at 4.2 and 5.4±0.2° are un-split and 100% intensity peak is present at 5.4±0.2°. As shown in FIG. 8, the crystalline form F of the Bortezomib is characterized by infrared absorption spectrum comprising the characteristic peaks approximately at 3267 $cm^{-1}$, 2952 $cm^{-1}$, 1660 $cm^{-1}$, 1511 $cm^{-1}$, and 1019 $cm^{-1}$. As shown in FIG. 9, the crystalline form F of the Bortezomib is characterized a melting point by the differential scanning calorimetry (DSC) at 121±2° C.

In summary, the present invention provides an industrially feasible, economically viable, commercially up-scalable process which may be safer for handling, less time consuming and which provides the product with improved yield and improved chemical purity.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A process for preparing Bortezomib, comprising the steps of:

(a) coupling a compound of formula I or its salt:

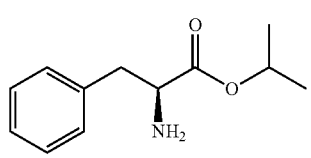

Formula I with a compound of formula II:

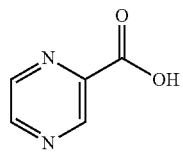

Formula II in the presence of a coupling agent and a base to provide a compound of formula III:

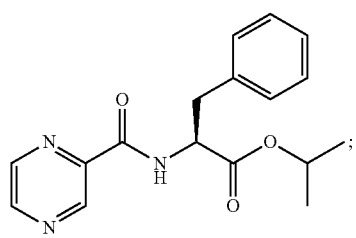

Formula III (b) converting the compound of formula III obtained in step (a) in the presence of the base to provide a compound of formula IV:

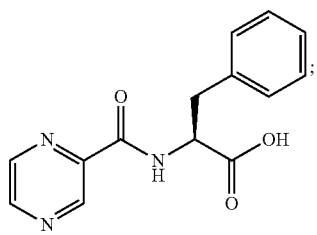

Formula IV (c) coupling the compound of formula IV obtained in step (b) with (1R)-3-methyl-1-[(3aS,4S,6S,7aR)-3a5,5-trimethylhexahydro-4,6 methano-1,3,2-benzodioxaborol-2-yl]butan-1-amine or its salt in the presence of the coupling agent and the base to provide an intermediate of (N-[(1S)-2-[[(1R)-1-[(3aS,4S,6S,7aR)-hexahydro-3a,5,5-trimethyl-4,6-methano-1,3,2-benzodioxaborol-2-yl]-3-methylbutylamino]-2-oxo-1-(phenylmethyl)ethyl]pyrazinecarboxamide without isolation; and (d) converting the intermediate obtained in step (c) with 0.44N to 3.1N acid based on the weight of the compound of formula IV to provide a compound of formula V:

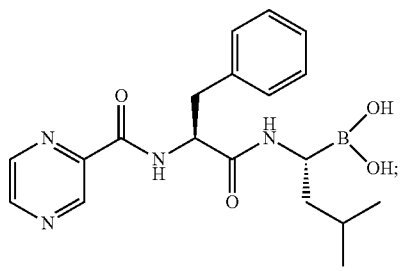

Formula V wherein the coupling agent is selected from the group consisting of O-benzotriazole-N,N,N',N'-tetramethyluronium-hexafluoro-phosphate (HBTU), 2-(6-chloro-1H-benzotriazole-1-yl)-1,1,3,3-tetramethylaminium hexafluorophosphate (HCTU), and N-(3-dimethylaminopropyl)-N'-ethylcarbodiimide hydrochloride (EDC); and wherein the base in solid, liquid or aqueous form is N,N-diisopropylethylamine (DIPEA).

2. The process according to claim 1, wherein the acid in step (d) is selected from the group consisting of an organic boronic acid and aqueous hydrochloric acid.

3. The process according to claim 1, wherein the compound of formula I or its salt is prepared by converting L-phenylalanine in the presence of 1.5 to 3.0 equivalent of thionyl chloride and isopropyl alcohol.

4. The process according to claim 1, wherein a mole ratio of the base to the compound of formula IV is 1.5 to 3.0.

5. The process according to claim 1, wherein a temperature of the step (a) is from about −15 to 10° C.

6. The process according to claim 1, wherein the compound of formula V has a purity level greater than 99.6% by HPLC.

7. The process according to claim 1, wherein the compound of formula V comprises less than 0.1% of S,S-isomer and R,R-isomer.

8. A process for preparing a crystalline form of the Bortezomib obtained from the process according to claim 1, comprising the steps of:
(a) dissolving the compound of formula V in a solution comprising tetrahydrofuran at 30-40° C.;
(b) cooling to 0 to −20° C. to precipitate a solid; and
(c) isolating the solid which is the crystalline form of the compound of formula V.

* * * * *